(12) United States Patent
Lee et al.

(10) Patent No.: US 10,183,140 B2
(45) Date of Patent: Jan. 22, 2019

(54) APPARATUS AND METHOD FOR LOCAL ANESTHESIA

(71) Applicants: AJOU UNIVERSITY INDUSTRY-ACADEMIC COOPERATION FOUNDATION, Gyeonggi-do (KR); UNIVERSITY-INDUSTRY COOPERATION GROUP OF KYUNG HEE UNIVERSITY, Gyeonggi-do (KR)

(72) Inventors: Kilyeon Lee, Seoul (KR); Moongu Lee, Gyeonggi-do (KR); Yongho Jeon, Gyeonggi-do (KR); Jaeseung Kim, Gyeonggi-do (KR)

(73) Assignees: AJOU UNIVERSITY INDUSTRY—ACADEMIC COOPERATION FOUNDATION (KR); UNIVERSITY—INDUSTRY COOPERATION GROUP OF KYUNG HEE UNIVERSITY (KR)

( * ) Notice: Subject to any disclaimer, the term of this patent is extended or adjusted under 35 U.S.C. 154(b) by 9 days.

(21) Appl. No.: 15/434,320

(22) Filed: Feb. 16, 2017

(65) Prior Publication Data

US 2017/0157357 A1 Jun. 8, 2017

Related U.S. Application Data

(63) Continuation of application No. PCT/KR2015/008672, filed on Aug. 19, 2015.

(30) Foreign Application Priority Data

Aug. 19, 2014 (KR) .................. 10-2014-0107606

(51) Int. Cl.
*A61M 5/178* (2006.01)
*A61M 5/00* (2006.01)
(Continued)

(52) U.S. Cl.
CPC ........ *A61M 19/00* (2013.01); *A61M 5/14212* (2013.01); *A61M 5/158* (2013.01);
(Continued)

(58) Field of Classification Search
CPC ............... A61M 11/007; A61M 19/00; A61M 2205/3334; A61M 2205/587;
(Continued)

(56) References Cited

U.S. PATENT DOCUMENTS 6,605,095 B2 * 8/2003 Grossman ............. A61B 90/13
356/399
6,623,457 B1 * 9/2003 Rosenberg ........... A61B 17/205
604/191

(Continued)

FOREIGN PATENT DOCUMENTS

JP 2001-137341 A 5/2001
KR 20-0399263 Y1 10/2005
(Continued)

OTHER PUBLICATIONS

International Search Report prepared by the Korean Intellectual Property Office dated Nov. 24, 2015, for International Application No. PCT/KR2015/008672.

*Primary Examiner* — Quynh-Nhu H. Vu
(74) *Attorney, Agent, or Firm* — Sheridan Ross P.C.

(57) ABSTRACT

The present invention relates to an apparatus and a method for local anesthesia and, more specifically, to an apparatus and a method for local anesthesia, which precisely indicate an anesthesia region and enable injection to be administered around the anesthesia region through a plurality of anesthe-
(Continued)

sia needles. According to the present invention, the fear and pain of a subject to be anesthetized can be reduced since the affected part of the subject to be anesthetized can be anesthetized by injecting a plurality of syringes all at once, and an injection can be precisely administered to a region at which an injection is to be administered since the affected part can be precisely indicated by a provided laser pointer.

11 Claims, 6 Drawing Sheets

(51) Int. Cl.
| | |
|---|---|
| *A61B 17/34* | (2006.01) |
| *A61M 5/32* | (2006.01) |
| *A61M 19/00* | (2006.01) |
| *A61M 5/42* | (2006.01) |
| *A61M 11/00* | (2006.01) |
| *A61M 5/142* | (2006.01) |
| *A61M 5/158* | (2006.01) |
| *A61M 5/168* | (2006.01) |

(52) U.S. Cl.
CPC .......... *A61M 5/16804* (2013.01); *A61M 5/42* (2013.01); *A61M 5/427* (2013.01); *A61M 11/007* (2014.02); *A61M 2205/3334* (2013.01); *A61M 2205/587* (2013.01); *A61M 2209/082* (2013.01)

(58) Field of Classification Search
CPC ........ A61M 2209/082; A61M 5/14212; A61M 5/158; A61M 5/16804; A61M 5/427
See application file for complete search history.

(56) References Cited

U.S. PATENT DOCUMENTS

| | | | | |
|---|---|---|---|---|
| 6,689,103 | B1* | 2/2004 | Palasis | A61B 17/3207 604/173 |
| 2004/0059285 | A1* | 3/2004 | Mathiesen | A61N 1/08 604/65 |
| 2004/0106934 | A1 | 6/2004 | Grossman | |
| 2007/0038181 | A1* | 2/2007 | Melamud | A61B 17/3478 604/158 |
| 2007/0162094 | A1* | 7/2007 | Goldman | A61B 5/0059 607/89 |
| 2007/0270710 | A1* | 11/2007 | Frass | A61B 10/0045 600/567 |
| 2012/0259219 | A1* | 10/2012 | Sheldon | A61B 17/3403 600/439 |
| 2014/0114279 | A1* | 4/2014 | Klinghoffer | A61M 5/1408 604/506 |
| 2014/0249504 | A1* | 9/2014 | Franklin | A61M 25/06 604/507 |
| 2015/0080844 | A1* | 3/2015 | Donovan | A61M 5/16854 604/505 |

FOREIGN PATENT DOCUMENTS

| | | |
|---|---|---|
| KR | 10-2006-0040053 | 10/2006 |
| KR | 10-1017392 | 2/2011 |
| KR | 10-2012-0041671 A | 5/2012 |
| KR | 10-2012-0093292 A | 8/2012 |
| KR | 10-2011-0030038 | 2/2013 |

* cited by examiner

APPARATUS AND METHOD FOR LOCAL ANESTHESIA

CROSS REFERENCE TO RELATED APPLICATIONS

This application is a continuation application of PCT Application No. PCT/KR2015/008672 having an international filing date of 19 Aug. 2015, which PCT application claimed the benefit of Korean Patent Application No. 10-2014-0107606 filed on 19 Aug. 2014, the disclosures of each of which are incorporated herein by reference.

BACKGROUND OF THE INVENTION

1. Field of the Invention

The present invention relates to an apparatus and a method for local anesthesia, more precisely an apparatus and a method for local anesthesia particularly indicating exactly an anesthesia region and enabling the injection to be administered around the anesthesia region through a plurality of anesthesia needles.

2. Description of the Related Art

Anesthesia indicates unconsciousness, painless, or elimination of body reaction that might interrupt operation. Anesthesia has always been with the history of mankind. In particular, anesthesiology (anesthesia science) has made remarkable progress since ether was used for general anesthesia in the 16th century.

In general, if anesthesia includes all of the unconsciousness, painless, and elimination of body reaction that might interrupt operation above, it is called general anesthesia. If anesthesia only works for a local area without losing consciousness, it is called local anesthesia or regional anesthesia.

Regional anesthesia includes spinal anesthesia, epidural anesthesia, and local anesthesia, etc. Epidural anesthesia is divided according to the region where an anesthetic drug is administered by an injection needle into thoracic epidural anesthesia, lumbar epidural anesthesia, and caudal epidural anesthesia. Regional anesthesia includes infiltration anesthesia, field block anesthesia, and peripheral nerve block anesthesia, etc.

Spinal anesthesia, epidural anesthesia, and caudal anesthesia are old anesthetic methods which have been used even before the development of anesthesia devices because they can be performed without complicated equipments, and are still frequently performed.

Recently, the development of new local anesthetics, the use of opioids, and the importance of acute and chronic pain management have become more common. According to the recent development of new local anesthetics and the use of opioids, along with the increasing interest on acute and chronic pain control, the anesthetic methods above are being more common. Spinal anesthesia is also called subarachnoid anesthesia because it is the method of administering local anesthetics to the cerebro-spinal fluid (CSF) in the subarachnoid space. Epidural anesthesia is a method of administering local anesthetics to the epidural space between the dura meter and the ligamentum flavum. In particular, the administration of local anesthetics into the epidural space of the sacrum is called caudal epidural anesthesia. When spinal anesthesia is performed, the injected local anesthetic spreads through the cerebrospinal fluid and the blocking zone is determined according to the spread range. At this time, only a small amount of local anesthetic is required. In the meantime, epidural anesthesia is only working in the limited region injected with local anesthetics, and requires a large amount of local anesthetics, compared with spinal anesthesia. Epidural anesthesia is working slowly but is able to maintain the anesthetic status for a long time by injecting local anesthetics through a catheter.

The methods for anesthesia above are called regional anesthesia because they only anesthetize a part of the body, or they are called conduction block because they block the neural pathway without losing consciousness of the patient. These methods for local anesthesia can avoid side effects or complications accompanied by general anesthesia and do not cause pain in patients after surgery.

However, for the regional anesthesia, multiple injections of anesthetics are required which causes pain. To solve the problem, the present inventors have proposed an apparatus and a method for local anesthesia which can accurately indicate the affected part of an anesthetic object and can reduce pain during anesthesia.

SUMMARY OF THE INVENTION

It is an object of the present invention to provide an apparatus and a method for local anesthesia which can insert a syringe with a plurality of needles to anesthetize the target region or around the target region for operation.

It is another object of the present invention to provide an apparatus and a method which can indicate precisely the target region for operation so that the injection can be administered precisely in the region.

To solve the problems above, the apparatus of the present invention can include a syringe fixing part wherein at least two fixing grooves spaced apart from each other on a hollow plate; a pointer fixing part attached on the syringe fixing part above and equipped with a pointer in order to indicate the target area through the empty space of the middle of the syringe fixing part; and at least two syringes that can be attached to and detached from the fixing grooves of the syringe fixing part.

In the syringe fixing part, the fixing grooves can be formed by connecting at least two circular grooves to each other in the radial direction of the syringe fixing part.

The position of the syringe mounted in the radial direction of the syringe fixing part can be changed on the fixing groove.

The syringe fixing part can be formed in the disc-type member.

The pointer can be either a laser pointer or an LED pointer

The pointer fixing part can include a mounting member that can be equipped on the outer side or the inner side of the syringe fixing part.

The pointer fixing part can include a hollow-type fixing member connected to the mounting member and having a center axis same to the empty space of the syringe fixing part.

The surface of the subject can be the affected part of the subject to be anesthetized.

The syringe can spray an anesthetic agent by electrical signal or by pressure of the fluid.

The apparatus of the invention can additionally include a supporting part that can be combined with the syringe fixing part or the pointer fixing part and can be fixed in the outer base in order to allow the movement of the syringe fixing part, the pointer fixing part, and the syringes in the possible range.

The supporting part can contain a clip member for the attachment onto the outer base and a supporting member that is formed in between the syringe fixing part or the pointer fixing part and the clip member to connect them each other and can control the location of the syringe fixing part or the pointer fixing part.

The apparatus of the invention can additionally include a pump control part that is connected to the syringe to spray anesthetics and can adjust the amount of the anesthetics.

The pump control part can control the flow rate of 0.5~7 ml/hr.

The method for local anesthesia of the present invention comprises the following steps:

fixing the syringe filled with anesthetics in the syringe fixing part to fit the affected area of a patient;

fixing the pointer to the pointer fixing part;

fixing the clip member to the outer base;

aligning the pointer to the affected part of a subject to be anesthetized;

inserting the syringe needle through the skin around the affected area of a subject to be anesthetized by moving the syringe fixing part;

injecting anesthetics to the subject to be anesthetized through the syringe by operating the pump control part; and retrieving the inserted syringe needle out of the subject by separating the syringe fixing part from the subject.

The pointer can be a light emitting device.

The subject to be anesthetized can be a subject for the inferior rectal nerve local anesthesia.

In the step of injecting anesthetics, the anesthetics can be injected at 0.5~7 ml/hr.

ADVANTAGEOUS EFFECT

According to the present invention, the fear and pain of a subject to be anesthetized can be reduced since the affected part of the subject to be anesthetized can be anesthetized by injecting a plurality of syringes all at once.

The injection can be precisely administered to the target region since the affected part can be precisely indicated by the laser pointer equipped in the apparatus.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Hereinafter, the apparatus and the method for local anesthesia of the present invention are described in more detail with the attached figures. The organization and operation of the apparatus and the method of the invention shown and described in the figures are presented as at least one example and therefore the technical idea and the core organization and operation of the apparatus and the method of the invention are not limited thereto.

The terms used in this invention are selected among the general terms widely used in these days with considering the functions of the invention, but can be modified by the intention or convention of those in the art or the advent of new technology. Some specific terms selected by the present inventors are also included, which would be precisely indicated in the description of the invention. Therefore, the terms used in this invention are not just names but they are defined based on the original meaning of the term and the idea of the present invention overall.

The present invention provides an apparatus for local anesthesia composed of a syringe fixing part wherein at least two fixing grooves spaced apart from each other on a hollow plate; a pointer fixing part attached on the syringe fixing part above and equipped with a pointer in order to indicate the target area through the empty space of the middle of the syringe fixing part; and at least two syringes that can be attached to and detached from the fixing grooves of the syringe fixing part.

Hereinafter, the apparatus for local anesthesia according to an example of the present invention is described in more detail with the attached figures.

Figure 1:
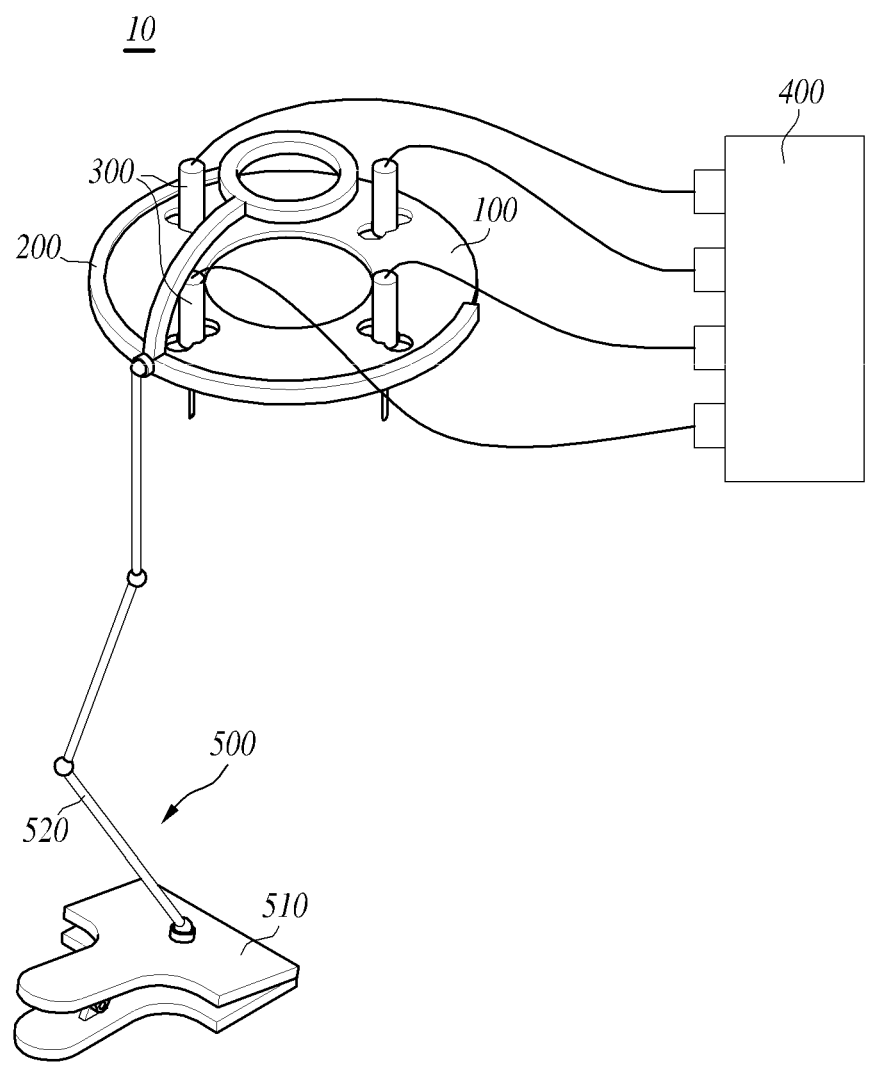
FIG. 1 is a diagram illustrating the apparatus for local anesthesia according to an example of the present invention.
Figure 2:
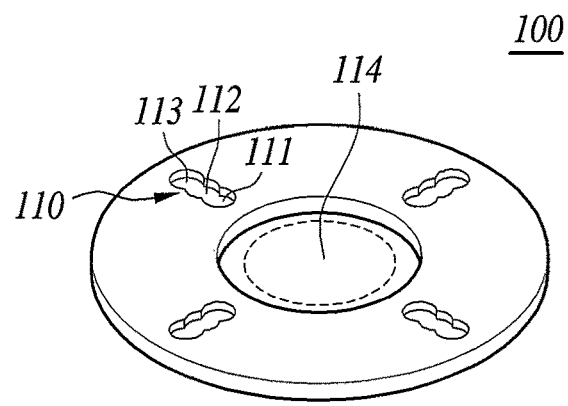
FIG. 2 is a diagram illustrating the syringe fixing part of the apparatus for local anesthesia according to an example of the present invention.
Figure 3:
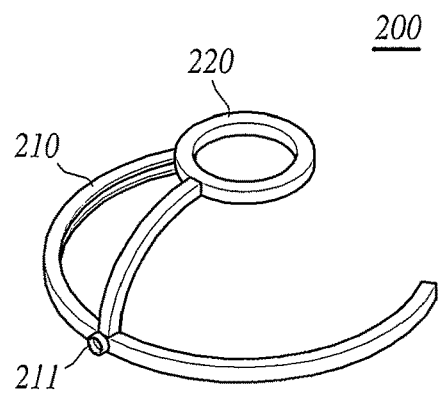
FIG. 3 is a diagram illustrating the pointer fixing part of the apparatus for local anesthesia according to an example of the present invention.
Figure 4:
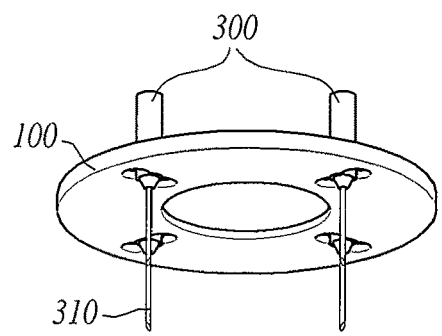
FIG. 4 is a diagram illustrating the syringes fixed on the syringe fixing part of the apparatus for local anesthesia according to an example of the present invention.
Figure 5:
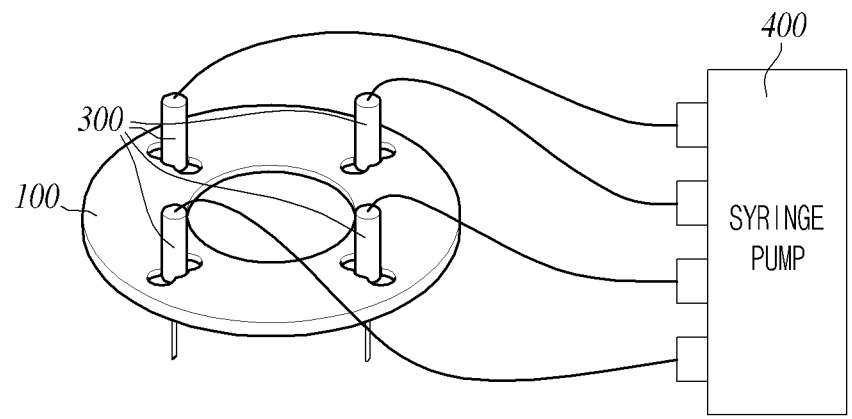
FIG. 5 is a diagram illustrating the syringes connected to the pump control part of the apparatus for local anesthesia according to an example of the present invention.

FIG. 1 is a diagram illustrating the apparatus for local anesthesia according to an example of the present invention. FIG. 2 is a diagram illustrating the syringe fixing part of the apparatus for local anesthesia according to an example of the present invention. FIG. 3 is a diagram illustrating the pointer fixing part of the apparatus for local anesthesia according to an example of the present invention. FIG. 4 is a diagram illustrating the syringes fixed on the syringe fixing part of the apparatus for local anesthesia according to an example of the present invention. FIG. 5 is a diagram illustrating the pump control part connected to the syringes shown in FIG. 4.

As shown in FIG. 1, the apparatus for local anesthesia (10) according to an example of the present invention is composed of the syringe fixing part (100), the pointer fixing part (200), the syringe (300), the pump control part (400), and the supporting part (500). At this time, the syringe fixing part (100) is shown as a circular plate, but can be any of polygonal plate forms, at least quadrangle.

As shown in FIG. 2, the syringe fixing part (100) is a hollow disc-shaped member that contains at least two fixing grooves (110). The fixing grooves (110) can be formed by connecting at least two, preferably three circular grooves (111, 112, and 113) to each other in the radial direction of the syringe fixing part (100). The fixing groove (110) is formed to attach the syringe (300) thereon. There is a empty space (114) in the middle of the syringe fixing part.

As shown in FIG. 3, the pointer fixing part (200) is attached to the outer side of the syringe fixing part (100). At this time, the pointer fixing part is attached to the outer side of the syringe fixing part (100) by the mounting member (210). In an example, the mounting member (210) can be equipped in the inside of the syringe fixing part (100). The supporter fixing part (211) can be formed on the one side of the mounting member. The supporter fixing part (211) can be formed not only on the pointer fixing part (200) but also on the syringe fixing part (100). In the case that the mounting member (210) is designed to be attached on the inside of the syringe fixing part (100), the supporter fixing part (211) is preferably attached on the syringe fixing part (100).

As shown in FIGS. 1 and 3, the supporting part (500) can be connected to the supporter fixing part (211). The supporting part (500) consists of the clip member (510) and the support member (520). The support member (520) is the bridge between the clip member (510) and the supporter fixing part (211). The clip member (510) is a fixing tool to fix on the outer base (not shown). At this time, the outer base can be such an object as a bed or a chair, etc. The support member (520) is designed for free up and down and right and left movement. In an example of the present invention, the three support members (520) are connected each other so as to rotate freely, by which the position of the pointer fixing part (200) connected to the supporting part (500) can be adjusted. Thus, the positions of the syringe fixing part (100) and the syringe (300) connected to the pointer fixing part (200) can be changed.

As shown in FIG. 3, the fixing member (220) is connected to the mounting member (210) so as to include the pointer (not shown). The pointer is a light emitting tool that generates light and indicates a target subject with the light, wherein the light is preferably laser or light emitting diode (LED). If LED is used for the pointer, the LED having excellent linearity is preferred. The pointer is attached onto the fixing member (220) in order to irradiate the laser beam through the empty space of the center of the syringe fixing part (100). The fixing member (220) is preferably equipped in the opposite direction of the needle (311) so as not to contact the affected part of a subject to be anesthetized.

As described hereinbefore, the syringes (300) can be equipped onto the fixing groove (110) of the syringe fixing part (100). As shown in FIG. 4, the position of the syringe can be adjusted according to the circular grooves (111, 112, and 113). The injection point differs from the patients or the affected parts, so the position of the syringe (300) is preferably adjusted therein.

As shown in FIG. 5, the pump control part (400) is connected to each syringe (300) fixed on the fixing groove (110) of the syringe fixing part (100) so that it can control the injection of each syringe separately or simultaneously. The syringe (300) is connected to the pump control part (400) electrically or physically, so that the dose of a drug for the injection can be controlled. If the syringe (300) is connected to the pump control part (400) electrically, the syringe (300) is controlled by the electrical signal generated in the pump control part (400), and if the syringe (300) is connected to the pump control part (400) physically, it can be controlled by the fluid pressure generated in the pump control part (400). The pump control part (400) can control the flow rate to be 0.5~7 ml/hr. If the flow rate controlled by the pump control part (400) is less than 0.5 ml/hr, the amount of the anesthetic injected would be too small to anesthetize a subject to be anesthetized. If the flow rate controlled by the pump control part (400) is more than 7 ml/hr, the amount of the anesthetic would be comparatively higher enough to cause pain in a patient. Therefore, the flow rate is preferably controlled by the pump control part in the range of 0.5~7 ml/hr, and more preferably 3~5 ml/hr, but not always limited thereto.

Figure 6:
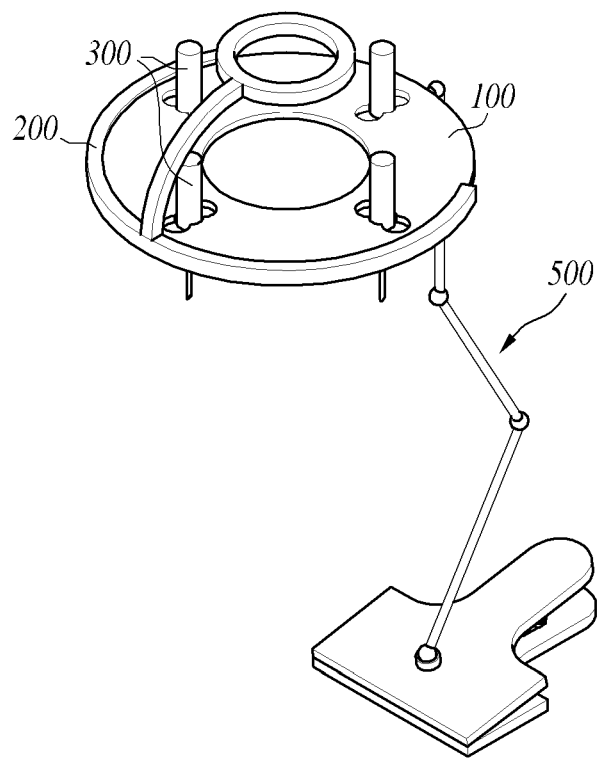
FIG. 6 is a diagram illustrating the apparatus for local anesthesia according to another example of the present invention.
Figure 7:
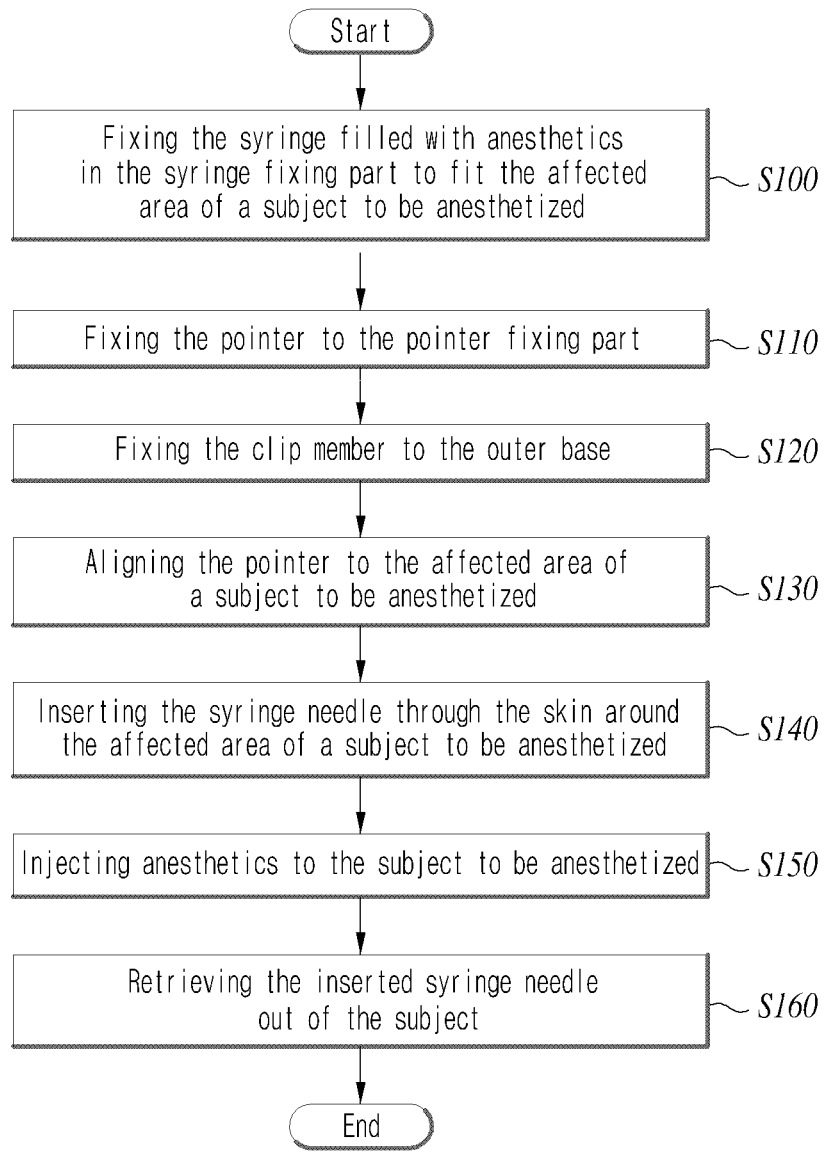
FIG. 7 is a flow chart illustrating the method for local anesthesia according to an example of the present invention.

FIG. 6 is a perspective view illustrating the apparatus for local anesthesia (20) according to another example of the present invention.

As shown in FIG. 6, the supporter fixing part (211) is equipped on the outer side of the syringe fixing part (100) to support the supporting part (500). At this time, the pointer fixing part (200) is attached on the syringe fixing part (100) but has a distance from the supporter fixing part (211).

The present invention provides a method for local anesthesia using the apparatus for local anesthesia of the invention, comprising the following steps: fixing the syringe filled with anesthetics in the syringe fixing part to fit the affected area of a patient; fixing the pointer to the pointer fixing part; fixing the clip member to the outer base; aligning the pointer to the affected part of a subject to be anesthetized; inserting the syringe needle through the skin around the affected area of a subject to be anesthetized by moving the syringe fixing part; injecting anesthetics to the subject to be anesthetized through the syringe by operating the pump control part; and retrieving the inserted syringe needle out of the subject by separating the syringe fixing part from the subject.

Hereinafter, the method for local anesthetized according to an example of the present invention is described in more detail.

First, the syringe filled with anesthetics is fixed in the syringe fixing part with adjusting the position to fit the affected area (S100). The anesthetic is individually packed in each syringe separately positioned around the affected area of a subject to be anesthetized. The injection position can vary from a subject, so it is preferred to adjust the position to an appropriate position according to the subject to be anesthetized.

Next, the pointer is fixed to the pointer fixing part (S110). At this time the pointer is fixed in the fixing member of the pointer fixing part. The pointer is a light emitting tool. For the pointer, a laser pointer without being scattered to many directions and having linearity is preferably used.

Figure 8:
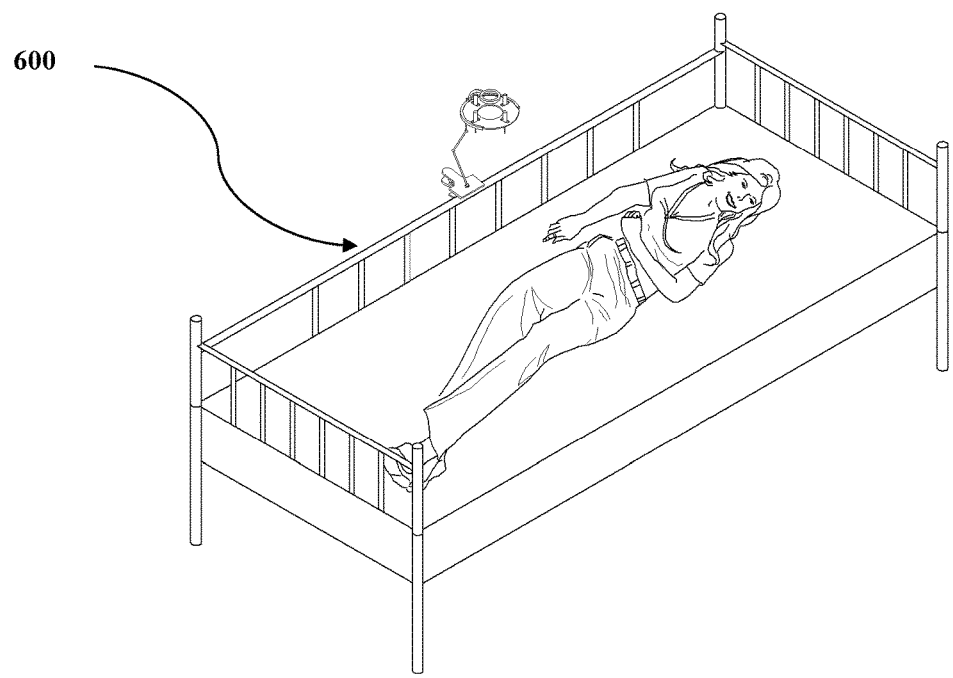
FIG. 8 is a diagram illustrating the step of fixing the clip member onto the outer base in the method for local anesthesia according to an example of the present invention.

Next, the clip member is fixed to the outer base (S120). As shown in FIG. 8, the outer base (600) can be an object located in the outside such as a bed or a chair, and any object form where the clip member can be fixed is accepted.

Next, the pointer is aligned to the affected area of a subject to be anesthetized by irradiating the pointer (S130). The target for anesthesia can be the inferior rectal nerve region herein, but not always limited thereto.

The laser beam irradiated from the pointer directs to the affected area but is not supposed to affect the area. The syringe can also be aligned with the arrangement of the laser beam for the affected area.

Figure 9:
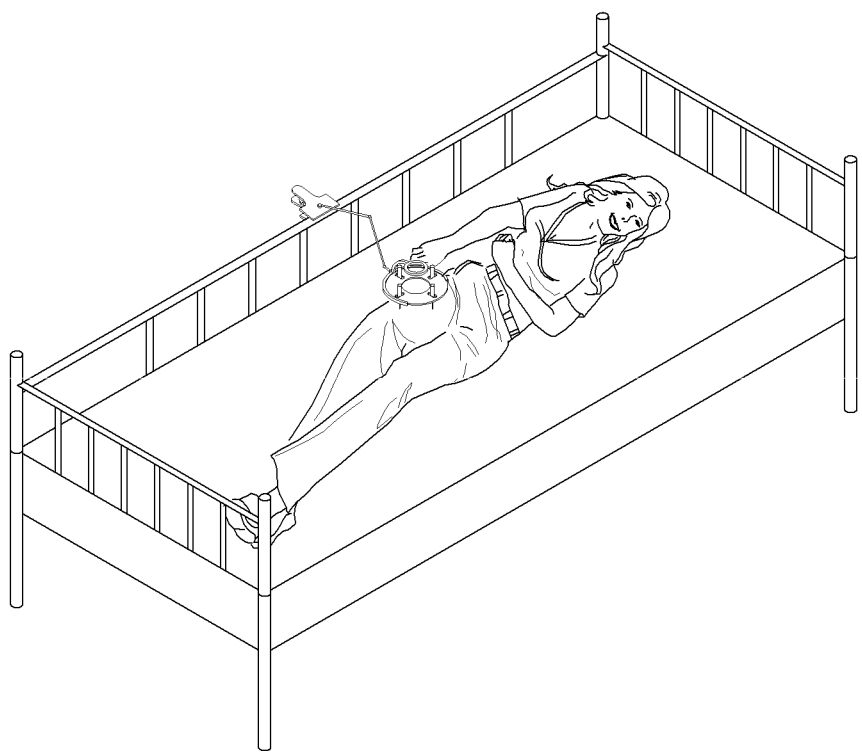
FIG. 9 is a diagram illustrating the step of inserting the syringe needle through the skin around the affected area of a subject to be anesthetized in the method for local anesthesia according to an example of the present invention.

Next, the syringe needle is inserted in the skin around the affected area of a subject to be anesthetized by moving the syringe fixing part (S140). As shown in FIG. 9, the syringe fixing part is moved by the support member that is designed for free rotation. The pointer aligned in the above step (S130) can be adjusted vertically to the affected area, but not always limited thereto. The irradiation of the laser beam from the pointer continues and the syringe is inserted in the skin around the affected area of a subject by moving the syringe fixing part carefully not to divert the laser beam from the affected area.

Next, anesthetic is injected into the subject to be anesthetized through the syringe by operating the pump control part (S150). The pump control part generates electrical signals or physical signals, through which the anesthetic can be injected in the inside of the body of a subject to be anesthetized. The dose of the anesthetic can be regulated by the pump control part. Also in the step (S150), the flow rate of the anesthetic is regulated in the range of 0.5~7 ml/hr. If the flow rate controlled by the pump control part is less than 0.5 ml/hr, the amount of the anesthetic injected would be too small to anesthetize a subject to be anesthetized. On the other hand, if the flow rate controlled by the pump control part is more than 7 ml/hr, the amount of the anesthetic would be comparatively higher enough to cause pain in a patient. Therefore, the flow rate is preferably controlled by the pump control part in the range of 0.5~7 ml/hr, and more preferably 3~5 ml/hr, but not always limited thereto.

The syringe needle inserted in the body of a subject to be anesthetized is taken out by separating the syringe fixing part from the subject (S160).

As described hereinbefore, the method of the invention is efficient in anesthetizing the affected area of a subject to be anesthetized by injecting a plurality of syringes all at once, so that the fear and pain of the subject can be reduced. Also, the method can precisely indicate the affected area with the equipped laser pointer, suggesting that the accurate injection is expected.

BRIEF DESCRIPTION OF THE MARK OF DRAWINGS

100: syringe fixing part
110: fixing groove
111: circular groove
200: pointer fixing part
210: mounting member
211: supporter fixing part
220: fixing member
300: syringe
310: needle
400: pump control part
410: connecting device
500: supporting part
510: clip member
520: support member
600: outer base Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. An apparatus for local anesthesia composed of:
    a syringe fixing part wherein at least two fixing grooves are spaced apart from each other on a hollow plate;
    a pointer fixing part attached on the syringe fixing part and adapted to be equipped with a laser pointer or a LED pointer in order to indicate a target area through a empty space in the middle of the syringe fixing part; and
    at least two syringes that can be attached to and detached from the fixing grooves of the syringe fixing part.

2. The apparatus for local anesthesia according to claim 1, wherein at least two circular grooves are connected in a radial direction of the syringe fixing part to form the fixing grooves of the syringe fixing part.

3. The apparatus for local anesthesia according to claim 2, wherein the at least two syringes are attached in a radial direction of the syringe fixing part and can be changed on the fixing groove.

4. The apparatus for local anesthesia according to claim 1, wherein the syringe fixing part is made of a disc-type member.

5. The apparatus for local anesthesia according to claim 1, wherein the pointer fixing part includes a mounting member that can be equipped on an outer side of the syringe fixing part.

6. The apparatus for local anesthesia according to claim 5, wherein the pointer fixing part includes a hollow-type fixing member connected to the mounting member and having a center axis same to the empty space of the middle of the syringe fixing part.

7. The apparatus for local anesthesia according to claim 1, wherein the target area is an affected part of a subject to be anesthetized.

8. The apparatus for local anesthesia according to claim 1, wherein the syringe is a tool to spray anesthetics by electrical signal or by pressure of the fluid.

9. The apparatus for local anesthesia according to claim 1, wherein the apparatus additionally includes a supporting part that can be combined with the syringe fixing part or the pointer fixing part and can be fixed in an outer base in order to allow the movement of the syringe fixing part, the pointer fixing part, and the syringes, and wherein the supporting part contains a clip member for an attachment onto the outer base and a supporting member that is formed in between the syringe fixing part or the pointer fixing part and the clip member to connect them to each other and can control a location of the syringe fixing part or the pointer fixing part.

10. The apparatus for local anesthesia according to claim 1, wherein the apparatus additionally includes a pump control part that is connected to the syringe to spray anesthetics and can adjust the amount of the anesthetics.

11. The apparatus for local anesthesia according to claim 10, wherein the pump control part controls the flow rate in the range of 0.5~7 ml/hr.

* * * * *